United States Patent [19]

Dorman et al.

[11] Patent Number: 5,260,503
[45] Date of Patent: Nov. 9, 1993

[54] HYBRID SORGHUM PLANT AND SEED 8358

[75] Inventors: Clarence Dorman, Taft, Tex.; John Krueger, Hutchinson, Kans.

[73] Assignee: Pioneer Hi-Bred International, Inc., Des Moines, Iowa

[21] Appl. No.: 796,899

[22] Filed: Nov. 25, 1991

Related U.S. Application Data

[63] Continuation of Ser. No. 60,450, Jun. 11, 1987.

[51] Int. Cl.[5] .......................... A01H 5/00; A01H 1/00
[52] U.S. Cl. .................................. 800/200; 800/250; 800/DIG. 55; 47/58
[58] Field of Search ....... 800/200, 205, 250, DIG. 55; 435/172.1, 172.3; 47/58

[56] References Cited

PUBLICATIONS

House, Leland R. (1982) "A Guide to Breeding Sorghum" ICRISAT, Andhra Pradesh India pp. 16-31.
1988 Grain Sorghum Performance Test in Texas—Neville P. Clarke Director. pp. 42-43.
Kresovich, S. et al., "Application of Cell and Tissue Culture Techniques for the Genetic Improvement of Sorghum" *Advances in Agronomy*, vol. 41, pp. 147-170 (1987).
1988 Grain Sorghum Performance Tests in Texas, Hybrid Taylor-Evans Seed T-E Y-77.
Bright & Jones (1985). *Cereal Tissue & Cell Culture.* Chapter 6, pp. 176-203. Martinus Hijnoff/Dr. W. Juns. Amtisdau.
J. M. Poehlman (1959) *Breeding Field Crops,* Henry Holt and Co., Inc., NY, pp. 290-291.
Kresovich, S. et al., "Application of Cell and Tissue Culture Techniques for the Genetic Improvement of Sorghum" *Advances in Agronomy*, vol. 41, pp. 147-170 (1987).

*Primary Examiner*—Gary Benzon
*Attorney, Agent, or Firm*—Sterne, Kessler, Goldstein & Fox

[57] ABSTRACT

According to the invention, there is provided a hybrid sorghum plant, designated 8358, produced by crossing two Pioneer Hi-Bred International, Inc., proprietary inbred lines of sorghum. This invention thus relates to the hybrid seed 8358, the hybrid plant produced from the seed, variants, mutants, and modifications of Pioneer hybrid 8358. This hybrid sorghum plant is characterized by superior yields, wide adaptation, excellent biotype C and E greenbug (*Schizaphis graminum*) resistance, excellent anthracnose (*Colletotricum graminicola*), resistance and excellent resistance to pathotype 1 and 3 downy mildew (*Sclerospora sorghi*) and races 1, 2, 3 and 4 of head smut (*Spaoelotheca reiliana*).

4 Claims, No Drawings

HYBRID SORGHUM PLANT AND SEED 8358

This is a continuation of application Ser. No. 07/060,450, filed Jun. 11, 1987.

FIELD OF THE INVENTION

This invention is in the field of plant breeding, specifically hybrid grain sorghum breeding.

BACKGROUND OF THE INVENTION

The goal of plant breeding is to combine in a single variety/hybrid various desirable traits of the parental lines. For field crops, these traits may include resistance to diseases and insects, tolerance to heat, drought and salt, reducing the time to crop maturity, greater yield and yield stability and better agronomic quality. With mechanical harvesting of many crops, uniformity of plant characteristics such as germination and stand establishment, growth rate, maturity, plant height and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous plants from differing backgrounds or two homozygous lines produce a uniform population of hybrid plants that may be heterozygous for many gene loci. A cross of two plants each heterozygous at a number of gene loci will produce a population of hybrid plants that differ genetically and will not be uniform.

Sorghum plants (*Sorghum bicolor* (L.) Moench) are bred in most cases by self pollination techniques. With the incorporation of male sterility (either genetic or cytoplasmic) cross pollination breeding techniques can also be utilized. Sorghum has a perfect flower with both male and female parts in the same flower located in the panicle. The flowers are usually in pairs on the panicle branches. Natural pollination occurs in sorghum when anthers (male flowers) open and pollen falls onto receptive stigma (female flowers). Because of the close proximity of male (anthers) and female (stigma) in the panicle, self pollination is very high (average 94%). Cross pollination may occur when wind or convection currents move pollen from the anthers of one plant to receptive stigma on another plant. Cross pollination is greatly enhanced with incorporation of male sterility which renders male flowers nonviable without affecting the female flowers. Successful pollination in the case of male sterile flowers requires cross pollination.

The development of sorghum hybrids requires the development of homozygous inbred lines, the crossing of these lines, and the evaluation of the crosses. Pedigree breeding methods, and to a lesser extent population breeding methods, are used to develop inbred lines from breeding populations. Breeding programs combine desirable traits from two or more inbred lines into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically, in the pedigree method of breeding five or more generations of selfing and selection is practiced. $F_1$ to $F_2$; $F_2$ to $F_3$; $F_3$ to $F_4$, $F_4$ to $F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate genes(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A hybrid sorghum variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $T_1$ F hybrid is more vigorous than its inbred parents. This hybrid vigor, or heterosis, can be manifested in many ways, including increased vegetative growth and increased yield.

The development of a hybrid sorghum variety involves five steps: (1) the formation of "restorer" and "non-restorer" germplasm pools; (2) the selection of superior plants from various "restorer" and "non-restorer" germplasm pools; (3) the selfing of the superior plants for several generations to produce a series of inbred lines, which although different from each other, each breed true and are highly uniform; (4) the conversion of inbred lines classified as non-restorers to cytoplasmic male sterile (CMS) forms, and (5) crossing the selected cytoplasmic male sterile (CMS) inbred lines with selected fertile inbred lines (restorer lines) to produce the hybrid progeny ($F_1$).

Because sorghum is normally a self pollinated plant and because both male and female flowers are in the same panicle, large numbers of hybrid seed can only be produced by using cytoplasmic male sterile (CMS) inbreds. Flowers of the CMS inbred are fertilized with pollen from a male fertile inbred carrying genes which restore male fertility in the hybrid ($F_1$) plants. An important consequence of the homozygosity and homogeneity of the inbred lines is that the hybrid between any two inbreds will always be the same. Once the inbreds that give the best hybrid have been identified, the hybrid seed can be reproduced indefinitely as long as the homogeneity of the inbred parent is maintained.

A single cross hybrid is produced when two inbred lines are crossed to produce the $_1$ progeny. Much of the hybrid vigor exhibited by $F_1$ hybrids is lost in the next generation ($F_2$). Consequently, seed from hybrid varieties is not used for planting stock.

Hybrid grain sorghum can be produced using wind to move the pollen. Alternating strips of the cytoplasmic male sterile inbred (female) and the male fertile inbred (male) are planted in the same field. Wind moves the pollen shed by the male inbred to receptive stigma on the female. Providing that there is sufficient isolation from sources of foreign sorghum pollen, the stigma of the male sterile inbred (female) will be fertilized only with pollen from the male fertile inbred (male). The resulting seed, born on the male sterile (female) plants is therefore hybrid and will form hybrid plants that have full fertility restored.

Grain sorghum is an important and valuable food and feed grain crop. In addition, its vegetative parts are used for forage, syrup and shelter Thus, a continuing goal of plant breeders is to develop stable high yielding sorghum hybrids that are agronomically sound. The reasons for this goal are obvious to maximize the amount of grain produced on the land used and to supply food for both animals and humans.

SUMMARY OF THE INVENTION

According to the invention, there is provided a hybrid grain sorghum plant, designated 8358, produced by crossing two Pioneer Hi-Bred International, Inc., proprietary inbred lines of sorghum. This invention thus relates to the hybrid seed 8358, the hybrid plant produced from the seed, variants, mutants and modifications of Pioneer hybrid 8358. This hybrid sorghum plant is characterized by superior yields, wide adaptation, excellent biotype C and E greenbug (*Schizaphis graminum* (Rondani) resistance, excellent anthracnose (*Colletotricum graminicola*) resistance and excellent resistance to pathotype 1 and 3 downy mildew (*Sclerospora sorghi*), and races 1, 2, 3 and 4 of head smut (*Sphacelotheca reiliana*).

DEFINITIONS

In the description and examples that follow, a number of terms are used herein. In order to provide a clear and consistent understanding of the specification and claims, including the scope to be given such terms, the following definitions are provided:

Predicted RM. This trait, predicted relative maturity (RM), for a hybrid is based on the number of days required for an inbred line or hybrid to shed pollen from the time of planting. The relative maturity rating is based on a known set of checks and utilizes standard linear regression analyses.

Yield/RM. This represents a rating of a hybrid yield compared to other hybrids of similar maturity or RM. A high score would indicate a hybrid with higher yield than other hybrids of the same maturity.

RM to Color. This trait for a hybrid is based on the number of days required for a hybrid to begin to show color development in the grain from the time of planting. The relative maturity rating is based on a known set of checks and utilizes standard linear regression analyses.

Yield (cwt/acre). The yield in cwt/acre is the actual yield of the grain at harvest adjusted to 13% moisture.

Percent Yield. The percent yield is the yield obtained from the hybrid in terms of percent of the mean for the experiment in which it was grown.

Yield Under Stress. This is a rating of the plants ability to produce grain under heat and drought stress conditions. A score of 9 would indicate near normal growth and grain yield and a score of 1 would indicate substantial yield reduction due to stress.

Drought Tolerance. This represents a rating for drought tolerance and is based on data obtained under stress. It is based on such factors as yield, plant health, lodging resistance and stay green. A high score would indicate a hybrid tolerant to drought stress.

Selection Index. The selection index gives a single measure of the hybrid's worth based on information for up to five traits. A sorghum breeder may utilize his or her own set of traits for the selection index. Two of the traits that are almost always included are yield and days to flower (maturity). The selection index data presented in the tables in the specification represent the mean values averaged across testing stations.

Moisture. The moisture is the actual percentage moisture of the grain at harvest.

Test Weight. This is the measure of the weight of the grain in pounds for a given volume (bushel) adjusted for percent moisture.

Dry Down. This represents the relative rate at which a hybrid will reach acceptable harvest moisture compared to other hybrids. A high score indicates a hybrid that dries relatively fast while a low score indicates a hybrid that dries slowly.

Head Exertion. This represents a rating for the length of the peduncle exposed between the base of the panicle (head) and the flag leaf of the plant. A high score indicates more distance between the flag leaf and the sorghum head while a low score indicates a short distance between the two. Head exertion is important for ease of combine harvesting.

Head Type. This represents a rating of the morphology of the sorghum panicle (head). A high score indicates an open panicle caused by either more distance between panicle branches or longer panicle branches. A low score indicates a more compact panicle caused by shorter panicle branches arranged more closely on the central rachis.

Stalk Lodging. This represents a rating of the percentage of plants that do not stalk lodge, i.e. stalk breakage above the ground caused by natural causes. This is a relative rating of a hybrid to other hybrids for standability.

Plant Height. This is a measure of the average height of the hybrid from the ground to the tip of the panicle and is measured in inches.

Root Lodging. This represents a rating of the percentage of plants that do not root lodge, i.e. those that lean from the vertical axis at an approximate 30 degree angle or greater without stalk breakage are considered to be root lodged. This is a relative rating of a hybrid to other hybrids for standability.

Sales Appearance. This represents a rating of the acceptability of the hybrid in the market place. It is a complex score including such factors as hybrid uniformity, appearance of yield, grain texture, grain color and general plant health. A high score indicates the hybrid would be readily accepted based on appearance only. A low score indicates hybrid acceptability to be marginal based on appearance only.

Days to Flower. The days to flower is the number of days required for an inbred line or hybrid to shed pollen from the time of planting.

Days to Color. The days to color is the number of days required for an inbred line or hybrid to begin grain coloring from the time of planting. Coloring of the grain is correlated with physiological maturity, thus days to color gives an estimate of the period required before a hybrid is ready for harvest.

Stay Green. Stay green is the measure of plant health near the time of harvest. A high score indicates better late-season plant health.

Weathering. This represents a rating of how well the exposed grains are able to retain normal seed quality when exposed to normal weather hazards and surface grain molds.

Salt Tolerance. This represents a rating of the plants ability to grow normally in soils having high sodium salt content. This is a relative rating of a hybrid to other hybrids for normal growth.

Rust Resistance. This is a visual rating based on the number of rust pustules present on the leaves and stem of the sorghum plant. A score of 9 would indicate the presence of few rust pustules.

Anthracnose Resistance. This is a visual rating based on the number of lesions caused by anthracnose infection. A score of 9 would indicate little necrosis and a score of 1 would indicate plant death as a result of anthracnose infection.

Head Smut Resistance (Races 1-4). This is a visual rating based on the percentage of smut infected plants. A score of 9 would indicate no infected plants and a score of 1 would indicate higher than 50% infected plants. Ratings are made for each race of head smut.

Downy Mildew Resistance (Pathotypes 1 and 3). This is a visual rating based on the percentage of downy mildew infected plants. A score of 9 indicates no infected plants. A score of 1 would indicate higher than 50% infected plants. Ratings are made for infection by each pathotype of the disease.

Gray Leaf Spot Resistance. This is a visual rating based on the number of gray leaf spot lesions present on the leaves and stem of the sorghum plant. A score of 9 would indicate the presence of few lesions.

Zonate Leaf Spot Resistance. This is a visual rating based on the number of zonate leaf spot lesions present on the leaves and stem of the sorghum plant. A score of 9 would indicate the presence of few lesions.

Leaf Burn Resistance. This is a visual rating based on the amount of tissue damage caused by exposure to insecticide sprays. A score of 9 would indicate minor leaf spotting and a score of 1 would indicate leaf death as a result of contact with insecticide spray.

Maize Dwarf Mosaic Virus Resistance. This is a visual rating based on the percentage of plants showing symptoms of virus infection. A score of 9 would indicate no plants with virus symptoms and a 1 would indicate a high percentage of plants showing symptoms of virus infection such as stunting, red leaf symptoms or leaf mottling.

Midge Resistance. This is a visual rating based on the percentage of seed set in the panicle in the presence of large numbers of midge adults. A score of 9 would indicate near normal seed set and a score of 1 would indicate no seed set in the head due to midge damage.

Chinch Bug Resistance. This is a visual rating based on the plants ability to grow normally when infested with large numbers of chinch bugs. A score of 9 would indicate normal growth and a score of 1 would indicate severe plant stunting and death.

Biotype C Greenbug Resistance. This is a visual rating based on the amount of necrosis on leaves and stems caused by biotype C greenbug feeding. A score of 9 would indicate no leaf or stem damage as a result of greenbug feeding.

Biotype E Greenbug Resistance. This is a visual rating based on plant seedlings ability to continue growing when infested with large numbers of biotype E greenbugs. A score of 9 indicates normal growth and a score of 1 indicates seedling death.

DETAILED DESCRIPTION OF THE INVENTION

Hybrid 8358 is a single cross made with Pioneer Hi-Bred proprietary sorghum inbred lines PH210 and PH232.

To produce 8358, inbred PH210 must be used as the female parent of the cross and inbred PH232 must be used as the male parent of the cross. Production planting should be timed so that the male pollen is shed at the same time that the female stigma are receptive to the pollen. The male inbred will flower and shed pollen 3-6 days earlier than the female flowers and becomes receptive to pollen. Therefore, the planting of the male inbred should be delayed 3-6 days to obtain maximum pollination with the male inbred. The hybrid grain sorghum seed 8358 produced by this cross can then be planted to produce the hybrid plant.

8358 is a late flowering hybrid, broadly adapted to the majority of the sorghum growing areas of the United States. This hybrid has high yield, excellent resistance to pathotype 1 and 3 downy mildew, races 1-4 of head smut and anthracnose. It is also resistant to biotype C and E greenbugs. The hybrid has good stalk and root strength. It is average in height with adequate head exertion and semi-open panicles. Test weight, stay green and weathering qualities are only average. The hybrid tends to flower late and then move to maturity very quickly. This ability contributes to its wide area of adaptation and allows it to be grown in states as far north as Nebraska. The hybrid is rated as a 74 RM hybrid based on days to flower and as a 71 RM hybrid based on days to color.

This hybrid has the following characteristics based on descriptive data collected at Plainview, Texas:

| A. | Maturity | |
| --- | --- | --- |
| | Days to flower | 73 |
| | Days to color | 98 |
| B. | Plant | |
| | Height (to panicle tip) | 45 cm |
| | Head exertion | 3-6 inches |
| | Plant color | Purple |
| | Number of tillers | 2-3 |
| | Cytoplasm type | Male Sterile (A1) |
| C. | Leaf | |
| | Width | 4 inches |
| | Length | 21 inches |
| | No. per main stalk | 11 |
| | Midrib color | Cloudy |
| | Color pattern | Solid |
| | Attitude | Horizontal |
| | Color | Dark green |
| D. | Panicle | |
| | Head type | Semi-open |
| | Panicle length | 5.7 inches |
| | Panicle shape | Cylindrical |
| | Panicle branches | Erect |
| | Panicle branch length | 3 inches |
| | Glume color | Red |
| | Awns | Absent |

| | -continued | |
|---|---|---|
| E. | Kernel | |
| | Seed size | 14,000–16,000/pound |
| | Pericarp color | Red |
| | Pericarp | Opaque |
| | Testa | Absent |
| | Endosperm color | White |
| | Endosperm texture | Corneous |
| F. | Disease Resistance | |
| | Downy mildew - pathotype 1 | Tolerant |
| | Downy mildew - pathotype 3 | Tolerant |
| | Maize dwarf mosaic virus | Tolerant |
| | Head smut - Race 1 | Tolerant |
| | Head smut - Race 2 | Tolerant |
| | Head smut - Race 3 | Tolerant |
| | Head smut - Race 4 | Tolerant |
| | Gray leaf spot | Intermediate |
| | Zonate leaf spot | Intermediate |
| | Anthracnose | Tolerant |
| | Rust | Intermediate |
| | Charcoal rot | Tolerant |
| | Fusarium stalk rot | Tolerant |
| G. | Insect Resistance | |
| | Greenbugs - biotype C | Tolerant |
| | Greenbugs - biotype E | Tolerant |
| | Chinch bugs | Susceptible |
| | Sorghum midge | Susceptible |

This invention includes the hybrid sorghum seed of 8358, the hybrid grain sorghum plant produced from the hybrid sorghum seed, and variants, modification and mutants of 8358.

The terms variants, modification and mutant refer to a hybrid seed or a plant produced by that hybrid seed which is phenotypically similar to 8358.

As used herein, the term "plant" includes plant cells, plant protoplasts, plant cell or tissue culture from which sorghum plants can be regenerated, plant calli, plant clumps and plant cells that are intact in plants or parts of plants such as flowers, kernels, panicles, leaves, stalks and the like. Sorghum tissue culture techniques are described in Bright and Jones, *Cereal Tissue and Cell Culture*, chapter 6, (Martinus Nijnoff/Dr. W. Junk, Amsterdam) on pages 176-203.

USES OF SORGHUM

Sorghum is used as livestock feed, as human food, and as raw material in industry. The most common use of sorghum grain in the United States is as livestock feed, primarily to beef cattle, dairy cattle, hogs and poultry. The sorghum plant is also used as livestock feed in the form of fodder, silage, hay and pasture.

Sorghum grain is most important as human food in areas outside the United States. In these areas, the grain is consumed in the form of bread, porridge, confectionaries and as an alcoholic beverage Grain sorghum may be ground into flour and either used directly or blended with wheat or corn flour in the preparation of food products. In addition to direct consumption of the grain, sorghum has long been used in many areas of the world to make beer. The of uses of sorghum, in addition to human consumption of kernels, include both products of dry—and wet—milling industries. The principle products of sorghum dry milling are grits, meal and flour. Starch and other extracts for food use can be provided by the wet milling process.

Sorghum provides a source of industrial raw material. Industrial uses are mainly from sorghum starch from the wet-milling industry and sorghum flour from the dry milling industry. Sorghum starch and flour have application in the paper and textile industries. Other industrial uses include applications in adhesives, building materials and as oil-well muds. Considerable amounts of sorghum, both grain and plant material, have been used in industrial alcohol production.

The seed of hybrid 8358, the hybrid sorghum plant produced from the seed, and various parts of the hybrid sorghum plant can be utilized for human food, livestock feed, and as a raw material for industry.

EXAMPLES

In the examples that follow, the traits and characteristics of 8358 are given. The history of this hybrid is as follows: the hybrid was first made at the Pioneer Hi-Bred International, Inc., Kingston Research Station in Kingston, Jamaica. Jamaica serves as a winter nursery site for research stations located in the United States. In the first year (1982), the experimental cross was tested in elite trials at the following sorghum research stations: Plainview, Texas; Hutchinson, Kansas; and York, Nebraska. Along with 8358; 1,940 non-specialty hybrids were evaluated. Of these 1,940 hybrids, 633 were wide area hybrids. A total of 81 replications or "reps" (one experiment/one location/one time) of yield test data were collected on the hybrid for some traits.

Additional hybrid seed was produced by several research stations including Plainview, Texas; Hutchinson, Kansas; and York, Nebraska. There was some seed produced for Plainview at Pioneer's Kingston, Jamaica location (winter nursery).

In the second year trials, the hybrid was tested widely in research trials, including testing in South Texas, and 90 replications of yield test data were collected on some agronomic traits. In conjunction with the yield testing, the hybrid was also included in disease and insect tests to determine its relative performance to known hybrids.

In the third year trials, 8358 was tested widely in research trials and 102 replications of data were collected for important traits. Again, the hybrid was evaluated in disease and insect tests.

In the fourth year, the hybrid was evaluated over a wide area in replicated tests. A total of 172 additional replications of data were collected in advanced trials. The hybrid was also widely tested in strip tests across the United States in its area of adaptation. Again, this hybrid was evaluated for tolerance to diseases and insects as compared to known hybrids.

In the examples that follow, the data collected on hybrid 8358 is presented for the key characteristics and traits. The scores are on a scale of 1 to 9, with 9 being the best unless otherwise indicated. The scores based on extensive testing are subjective in nature, but include input from expert sorghum researchers.

EXAMPLE I

Comparison of Various Sorghum Hybrid Characteristics

Comparison of the characteristics of 8358 were made against Pioneer brand hybrids 8333 and 8222, sorghum hybrids developed and marketed by applicant in the same maturity zone as 8358.

Comparison of the characteristics of 8358 was also made against Funks G1711 and FUNKS G522DR sorghum hybrids. The result of these comparisons are given in Tables IA through ID.

TABLE IA

COMPARISONS OF HYBRIDS 8358 AND FUNKS G522DR FROM PERIOD OF YEARS RESEARCH DATA

| HYBRID | PREDICTED RM | SELECTION INDEX | PERCENT YIELD | YIELD CWT/AC | MOISTURE | TEST WEIGHT | HEAD EXERTION | HEAD TYPE |
|---|---|---|---|---|---|---|---|---|
| REPS | 262 | 402 | 402 | 402 | 381 | 129 | 352 | 346 |
| 8358 | 73 | 103 | 103 | 55 | 102 | 101 | 97 | 99 |
| 8333 | 71 | 100 | 102 | 55 | 101 | 100 | 91 | 111 |
| DIFF. | 2 | 3 | 1 | 0 | 1 | 1 | 6 | 12 |

| HYBRID | STALK LODGING | PLANT HEIGHT | SALES LODGING | TO APPEARANCE | DAYS TO FLOWER | DAYS TO STAY COLOR | GREEN | WEATHERING |
|---|---|---|---|---|---|---|---|---|
| REPS | 75 | 345 | 21 | 420 | 408 | 305 | 18 | 12 |
| 8358 | 106 | 99 | 100 | 114 | 102 | 100 | 97 | 99 |
| 8333 | 107 | 97 | 94 | 98 | 101 | 102 | 107 | 102 |
| DIFF. | 1 | 2 | 6 | 16 | 1 | 2 | 10 | 3 |

| HYBRID | SALT TOLERANCE | RUST | ANTHRACNOSE | HEAD SMUT | DOWNY MILDEW PATH 1 | GRAY LEAF SPOT SCORE | LEAF BURN SCORE | ZONATE LEAF SPOT SCORE | MAIZE DWARF MOSAIC VIRUS |
|---|---|---|---|---|---|---|---|---|---|
| REPS | 6 | 23 | 14 | 8 | 16 | 1 | 4 | 16 | 2 |
| 8358 | 130 | 95 | 134 | 112 | 118 | 82 | 73 | 93 | 135 |
| 8333 | 111 | 124 | 81 | 110 | 109 | 123 | 77 | 124 | 77 |
| DIFF. | 19 | 29 | 53 | 2 | 9 | 41 | 4 | 31 | 58 |

STATIONS TESTED:
NORTH PLATTE, NEBRASKA
HUTCHINSON, KANSAS
PLAINVIEW, TEXAS
TAFT, TEXAS

TABLE IB

COMPARISONS OF HYBRIDS 8358 AND FUNKS G1711 FROM PERIOD OF YEARS RESEARCH DATA

| HYBRID | PREDICTED RM | SELECTION INDEX | PERCENT YIELD | YIELD CWT/AC | MOISTURE | TEST WEIGHT | HEAD EXERTION | HEAD TYPE |
|---|---|---|---|---|---|---|---|---|
| REPS | 127 | 225 | 225 | 225 | 210 | 99 | 205 | 205 |
| 8358 | 73 | 103 | 102 | 58 | 101 | 101 | 98 | 101 |
| G1711 | 72 | 105 | 105 | 60 | 101 | 100 | 95 | 88 |
| DIFF. | 1 | 2 | 3 | 2 | 0 | 1 | 3 | 13 |

| HYBRID | STALK LODGING | PLANT HEIGHT | ROOT LODGING | SALES APPEARANCE | DAYS TO FLOWER | DAYS TO COLOR | STAY GREEN | WEATHERING |
|---|---|---|---|---|---|---|---|---|
| REPS | 18 | 213 | 18 | 231 | 227 | 188 | 18 | 3 |
| 8358 | 108 | 98 | 100 | 106 | 101 | 99 | 98 | 101 |
| G1711 | 98 | 103 | 79 | 112 | 100 | 101 | 81 | 91 |
| DIFF. | 10 | 5 | 21 | 6 | 1 | 2 | 17 | 10 |

| HYBRID | SALT TOLERANCE | RUST | ANTHRACNOSE | HEAD SMUT | DOWNY MILDEW PATH 1 | GRAY LEAF SPOT SCORE | LEAF BURN SCORE | ZONATE LEAF SPOT SCORE | MAIZE DWARF MOSAIC VIRUS |
|---|---|---|---|---|---|---|---|---|---|
| REPS | 4 | 23 | 9 | 2 | 4 | 1 | 2 | 5 | 1 |
| 8358 | 130 | 102 | 134 | 112 | 118 | 82 | 73 | 93 | 135 |
| G1711 | 68 | 80 | 113 | 98 | 109 | 112 | 100 | 106 | 100 |
| DIFF. | 72 | 22 | 21 | 14 | 9 | 20 | 27 | 13 | 35 |

STATIONS TESTED:
NORTH PLATTE, NEBRASKA
HUTCHINSON, KANSAS
PLAINVIEW, TEXAS
TAFT, TEXAS

TABLE IC

COMPARISONS OF HYBRIDS 8358 AND 8222 FROM PERIOD OF YEARS RESEARCH DATA

| HYBRID | PREDICTED RM | SELECTION INDEX | PERCENT YIELD | YIELD CWT/AC | MOISTURE | TEST WEIGHT | HEAD EXERTION | HEAD TYPE |
|---|---|---|---|---|---|---|---|---|
| REPS | 118 | 192 | 192 | 192 | 177 | 51 | 166 | 166 |
| 8358 | 73 | 104 | 103 | 59 | 101 | 101 | 100 | 97 |
| 8222 | 73 | 101 | 103 | 59 | 101 | 102 | 90 | 100 |
| DIFF. | 0 | 3 | 0 | 0 | 0 | 1 | 10 | 3 |

| HYBRID | STALK LODGING | PLANT HEIGHT | ROOT LODGING | SALES APPEARANCE | DAYS TO FLOWER | DAYS TO COLOR | STAY GREEN | WEATHERING |
|---|---|---|---|---|---|---|---|---|
| REPS | 42 | 168 | 6 | 207 | 203 | 131 | 3 | 9 |
| 8358 | 105 | 99 | 87 | 114 | 102 | 99 | 114 | 97 |
| 8222 | 106 | 98 | 105 | 103 | 102 | 101 | 125 | 117 |

TABLE IC-continued
COMPARISONS OF HYBRIDS 8358 AND 8222 FROM PERIOD OF YEARS RESEARCH DATA

| | DIFF. | 1 | 1 | 18 | 11 | 0 | 2 | 11 | 20 |
|---|---|---|---|---|---|---|---|---|---|

| HYBRID | SALT TOLERANCE | RUST | ANTHRACNOSE | HEAD SMUT | DOWNY MILDEW PATH 1 | GRAY LEAF SPOT SCORE | LEAF BURN SCORE | ZONATE LEAF SPOT SCORE | MAIZE DWARF MOSAIC VIRUS |
|---|---|---|---|---|---|---|---|---|---|
| REPS | 3 | 2 | 12 | 2 | 4 | 1 | 4 | 4 | 1 |
| 8358 | 130 | 87 | 134 | 112 | 118 | 82 | 73 | 93 | 135 |
| 8222 | 125 | 134 | 104 | 107 | 104 | 75 | 103 | 143 | 174 |
| DIFF. | 5 | 47 | 30 | 5 | 14 | 7 | 30 | 50 | 39 |

STATIONS TESTED:
NORTH PLATTE, NEBRASKA
HUTCHINSON, KANSAS
PLAINVIEW, TEXAS
TAFT, TEXAS

TABLE ID
COMPARISONS OF HYBRIDS 8358 AND 8333 FROM PERIOD OF YEARS RESEARCH DATA

| HYBRID | PREDICTED RM | SELECTION INDEX | PERCENT YIELD | YIELD CWT/AC | MOISTURE | TEST WEIGHT | HEAD EXERTION | HEAD TYPE |
|---|---|---|---|---|---|---|---|---|
| REPS | 262 | 402 | 402 | 402 | 381 | 129 | 352 | 346 |
| 8358 | 73 | 103 | 103 | 55 | 102 | 101 | 97 | 99 |
| 8333 | 71 | 100 | 102 | 55 | 101 | 100 | 91 | 111 |
| DIFF. | 2 | 3 | 1 | 0 | 1 | 1 | 6 | 12 |

| HYBRID | STALK LODGING | PLANT HEIGHT | ROOT LODGING | SALES APPEARANCE | DAYS TO FLOWER | DAYS TO COLOR | STAY GREEN | WEATHERING |
|---|---|---|---|---|---|---|---|---|
| REPS | 75 | 345 | 21 | 420 | 408 | 305 | 18 | 12 |
| 8358 | 106 | 99 | 100 | 114 | 102 | 100 | 97 | 99 |
| 8333 | 107 | 97 | 94 | 98 | 101 | 102 | 107 | 102 |
| DIFF. | 1 | 2 | 6 | 16 | 1 | 2 | 10 | 3 |

| HYBRID | SALT TOLERANCE | RUST | ANTHRACNOSE | HEAD SMUT | DOWNY MILDEW PATH 1 | GRAY LEAF SPOT SCORE | LEAF BURN SCORE | ZONATE LEAF SPOT SCORE | MAIZE DWARF MOSAIC VIRUS |
|---|---|---|---|---|---|---|---|---|---|
| REPS | 6 | 23 | 14 | 8 | 16 | 1 | 4 | 16 | 2 |
| 8358 | 130 | 95 | 134 | 112 | 118 | 82 | 73 | 93 | 135 |
| 8333 | 111 | 124 | 81 | 110 | 109 | 123 | 77 | 124 | 77 |
| DIFF. | 19 | 29 | 53 | 2 | 9 | 41 | 4 | 31 | 58 |

STATIONS TESTED:
NORTH PLATTE, NEBRASKA
HUTCHINSON, KANSAS
PLAINVIEW, TEXAS
TAFT, TEXAS

EXAMPLE II

Strip Test Data

Comparison data was collected from strip tests that were grown by farmers. Each hybrid was grown in strips of 4, 6, 8, 12, etc. rows in fields depending on size of the planter used. The data were collected from strip tests that had the hybrids in the same field. At harvest, the grain was harvested from a measured area and weighed. The moisture percentage was determined to compute yield and bushels per acre was adjusted to 13% moisture. Each replication or "rep" represents a distinct field.

Comparison strip testing was done between 8358 and Pioneer brand 8333 and 8222. Comparison strip testing was also done between 8358 and Funks G1711 and Funks G522DR.

The results are presented in Tables IIA. Traits characterized on the strip test data in addition to those defined previously are as follows:

Number of Wins. For yield, this number represents the number of times a given hybrid won the comparison.

COMPARISONS OF HYBRID 8358 WITH 8222, 8333, FUNKS 522DR AND FUNKS 1711 FROM 1986 STRIP TEST DATA

| | No. Reps. | Yield Lbs/ac | No. of Wins | Moisture | Lodge Score | Test Weight |
|---|---|---|---|---|---|---|
| 8358 | 4 | 6962.5 | 1 | 14.7 | 9 | 61.0 |
| 8222 | | 7252.7 | 3 | 15.4 | 9 | 61.5 |
| 8358 | 58 | 6773 | 29 | 15.8 | 9 | 58.6 |
| 8333 | | 6765 | 29 | 15.6 | 8 | 58.4 |
| 8358 | 2 | 6203.7 | 2 | 13.9 | | 60.0 |
| Funks 522DR | | 5664.2 | 0 | 14.2 | | 59.5 |
| 8358 | 3 | 6798.4 | 1 | 14.2 | | 59.0 |
| Funks 1711 | | 6833.4 | 2 | 14.3 | | 60.0 |

EXAMPLE III

Comparison of Key Traits

Characteristics of hybrid 8358 were compared to Pioneer brand hybrids 8333 and 8222 for key traits. Table IIIA gives the comparison characteristics for 8358 compared to Pioneer brand hybrids 8333 and 8222. Table IIIB gives comparison characteristics for 8358 compared to Funks 522DR and Funks 1711 hybrids. These data were compiled utilizing the research data for each of the hybrids that are listed. The ratings given for most of the traits are on a 1 to 9 scale. In these cases, 9 would be outstanding, while a 1 would be poor for the given characteristic. The values are based on performance of the given hybrid relative to other Pioneer commercial and pre-commercial hybrids.

The traits characterized in Table IIIA and Table IIIB were defined previously. Disease and insect resistance are rated in Table IIIA and Table IIIB. A score of 9 indicates outstanding resistance, while a score of 1 indicates that the hybrid is very susceptible to the disease or insect given. The diseases and insects tested include pathotypes 1 and 3 of downy mildew, maize dwarf mosaic virus (MDMV), races 1-4 of head smut (head smut 1, head smut 2, etc), gray leaf spot, zonate leaf spot, anthracnose, rust, biotypes C and E greenbugs, chinch bugs and midge.

the phenotypic traits of resistance to pathotype I Downy mildew, resistance to pathotype III Downy mildew, resistance to biotype C Greenbug, resistance to biotype E Greenbug, and stalk lodging resistance.

2. A hybrid sorghum plant produced by the seed of claim 1, and seeds derived from said hybrid.

3. The hybrid sorghum plant of claim 2 wherein said hybrid sorghum plant comprises the phenotypic traits of resistance to pathotype I Downy mildew, resistance to pathotype III Downy mildew, resistance to biotype C Greenbug, resistance to biotype E Greenbug, and stalk lodging resistance.

4. A hybrid sorghum plant produced by the crossing of the two inbred lines of sorghum, PH210 and PH232, wherein said PH210 is a female inbred line and comprises the phenotypic traits of resistance to pathotype I Downy mildew and resistance to pathotype III Downy

TABLE IIIA

CHARACTERISTIC OF HYBRIDS 8358, 8333 AND 8222 FOR KEY TRAITS

| HYBRID | RM TO FLOWER | RM TO COLOR | YIELD/RM | YIELD UNDER STRESS | HEIGHT UNIFORMITY | DRY DOWN | STALK LODGING | ROOT LODGING |
|---|---|---|---|---|---|---|---|---|
| 8358 | 73 | 71 | 7 | 7 | 8 | 8 | 8 | 6 |
| 8333 | 72 | 72 | 7 | 6 | 9 | 5 | 7 | 6 |
| 8222 | 73 | 72 | 7 | 6 | 8 | 6 | 9 | 9 |

| HYBRID | STAY GREEN | DROUGHT TOLERANCE | DOWNY MILDEW PATH 1 | DOWNY MILDEW PATH 3 | MDMV | HEAD SMUT 1 | HEAD SMUT 2 | HEAD SMUT 3 | HEAD SMUT 4 |
|---|---|---|---|---|---|---|---|---|---|
| 8358 | 5 | 7 | 9 | 9 | 8 | 9 | 9 | 9 | |
| 8333 | 5 | 5 | 9 | 9 | 5 | 9 | 9 | 9 | 9 |
| 8222 | 7 | 5 | 9 | 9 | 9 | 9 | 9 | 9 | 9 |

| HYBRID | GRAY LEAF SPOT | ZONATE LEAF SPOT | ANTHRACNOSE | RUST | GREENBUGS BIO C | GREENBUGS BIO E | CHINCH BUGS | MIDGE |
|---|---|---|---|---|---|---|---|---|
| 8358 | 5 | 5 | 8 | 5 | 9 | 9 | 1 | 1 |
| 8333 | 7 | 7 | 4 | 7 | 9 | 3 | 1 | 1 |
| 8222 | 3 | 7 | 6 | 7 | 3 | 3 | 1 | 1 |

TABLE IIIB

CHARACTERISTIC OF HYBRIDS 8358, G1711 AND G522DR FOR KEY TRAITS

| HYBRID | RM TO FLOWER | RM TO COLOR | YIELD/RM | YIELD UNDER STRESS | HEIGHT UNIFORMITY | DRY DOWN | STALK LODGING | ROOT LODGING |
|---|---|---|---|---|---|---|---|---|
| 8358 | 73 | 71 | 7 | 7 | 8 | 8 | 8 | 6 |
| G1711 | 72 | 73 | 9 | 6 | 5 | 4 | 3 | 1 |
| G522DR | 71 | 71 | 7 | 7 | 6 | 5 | 7 | 7 |

| HYBRID | STAY GREEN | DROUGHT TOLERANCE | DOWNY MILDEW PATH 1 | DOWNY MILDEW PATH 3 | MDMV | HEAD SMUT 1 | HEAD SMUT 2 | HEAD SMUT 3 | HEAD SMUT 4 |
|---|---|---|---|---|---|---|---|---|---|
| 8358 | 5 | 7 | 9 | 9 | 8 | 9 | 9 | 9 | 9 |
| G1711 | 5 | 5 | 8 | 4 | 5 | 9 | 9 | 9 | 9 |
| G522DR | 5 | 6 | 8 | 2 | 8 | 9 | 9 | 9 | 9 |

| HYBRID | GRAY LEAF SPOT | ZONATE LEAF SPOT | ANTHRACNOSE | RUST | GREENBUGS BIO C | GREENBUGS BIO E | CHINCH BUGS | MIDGE |
|---|---|---|---|---|---|---|---|---|
| 8358 | 5 | 5 | 8 | 5 | 9 | 9 | 1 | 1 |
| G1711 | 7 | 7 | 4 | 3 | 8 | 1 | 1 | 1 |
| G522DR | 8 | 7 | 4 | 3 | 1 | 1 | 1 | 1 |

What is claimed is:

1. Hybrid sorghum seed designated 8358 wherein said seeds are capable of germinating into a plant comprising mildew.

* * * * *